(12) United States Patent
Noelke et al.

(10) Patent No.: US 7,040,581 B2
(45) Date of Patent: May 9, 2006

(54) COMFORT ENHANCER FOR A BREATHING APPARATUS

(75) Inventors: John G. Noelke, Ft. Pierce, FL (US); James F. Sowinski, Vero Beach, FL (US)

(73) Assignee: Sonotech, LLC, Vero Beach, FL (US)

( * ) Notice: Subject to any disclaimer, the term of this patent is extended or adjusted under 35 U.S.C. 154(b) by 92 days.

(21) Appl. No.: 10/776,729

(22) Filed: Feb. 10, 2004

(65) Prior Publication Data
US 2005/0173599 A1   Aug. 11, 2005

(51) Int. Cl.
*A62C 13/76* (2006.01)

(52) U.S. Cl. ............ 248/75; 5/646; 5/83; 5/503.1; 248/123.11

(58) Field of Classification Search ........... 248/75, 248/121, 122, 125.1, 125.2, 157, 158, 123.11, 248/161, 323, 176.1, 176.3, 328, 330.1, 431, 248/432, 188.8, 188.2; 636/24.1; 5/646; 239/281; 362/287
See application file for complete search history.

(56) References Cited

U.S. PATENT DOCUMENTS

| 2,748,236 | A |   | 5/1956  | Landis et al. |
| 2,978,217 | A |   | 4/1961  | Gunderson |
| 2,997,242 | A | * | 8/1961  | Grosholz ............... 239/281 |
| 3,464,411 | A |   | 9/1969  | Martinez |
| 4,238,096 | A |   | 12/1980 | Dvorachek |
| 5,279,486 | A |   | 1/1994  | Harmon |
| 5,836,361 | A |   | 11/1998 | Koncsek |
| 6,019,484 | A | * | 2/2000  | Seyler ................ 362/287 |
| 6,516,802 | B1|   | 2/2003  | Hansen et al. |

* cited by examiner

*Primary Examiner*—Robert P. Olszewski
*Assistant Examiner*—Todd M. Epps
(74) *Attorney, Agent, or Firm*—McHale & Slavin PA

(57) ABSTRACT

A comfort enhancer for supporting a CPAP mask and hose is designed to be portable and deployed on any standard bed. The support has a bi-pod base placed between the mattress and the inner spring of the bed. An upright pole, removably attached to the base and adjustable in height, carries hose clamps. A bracket attached to the top of the pole has a cantilever arm pivotally attached by a spring loaded pulley. The cantilever arm also carries hose clamps. The comfort enhancer supports the air hose at a distance from the bed and above the head of the user allowing the hose descend vertically to the user. The cantilever arm pivots to compensate for the movement of the mask and the spring loaded pulley absorbs the shock to the line.

8 Claims, 4 Drawing Sheets

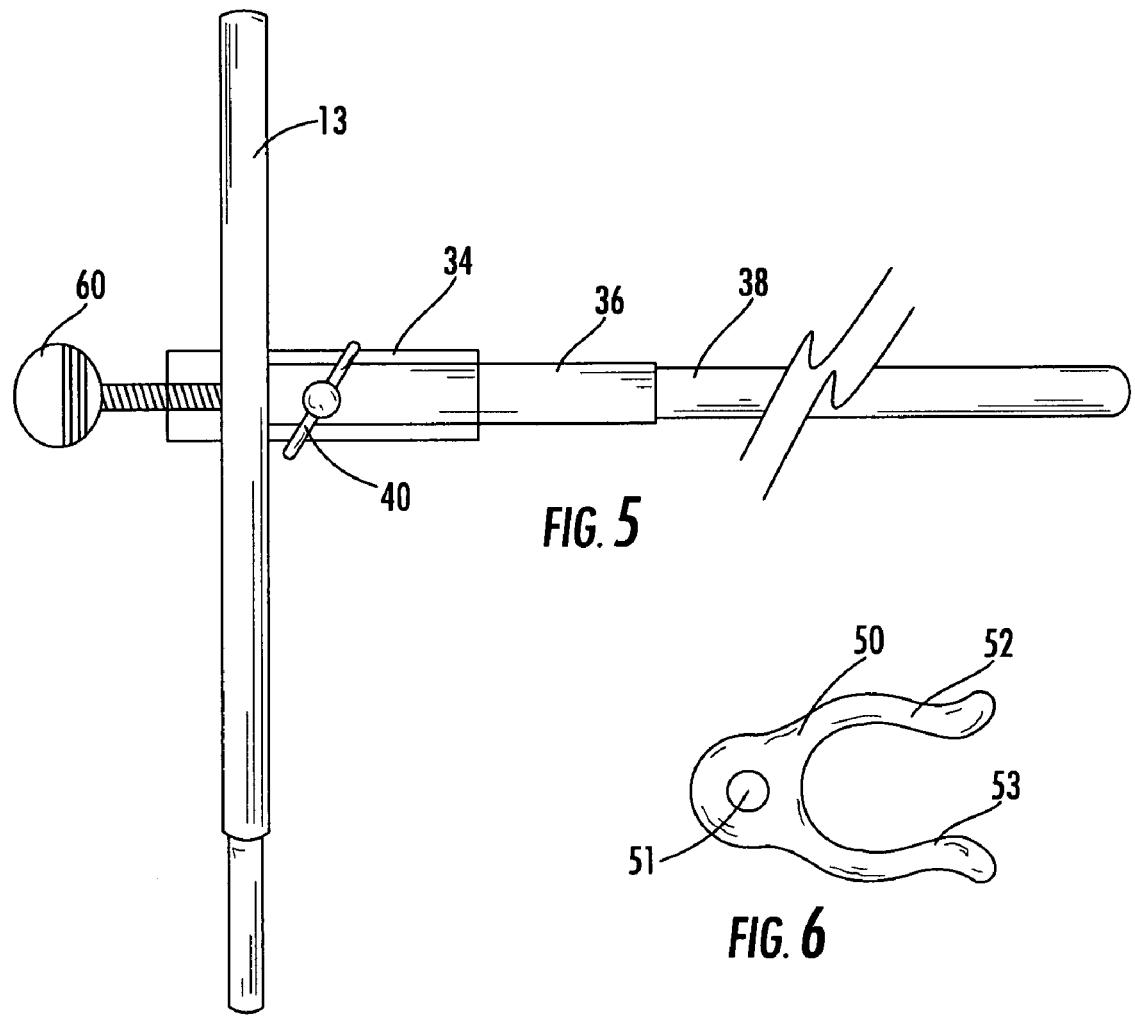

COMFORT ENHANCER FOR A BREATHING APPARATUS

BACKGROUND OF THE INVENTION

1. Field of the Invention

This invention relates to the field of breathing disorders and, more particularly, to apparatus used to treat sleep apnea. However, the invention relates to any tubular supply device for bedridden patients.

2. Description of the Prior Art

The use of positive pressure respirators to treat sleep apnea is known, as taught by Hansen et al, U.S. Pat. No. 6,516,802, which discloses a device to control a hose in a CPAP, continuous positive airway pressure, system.

A product on the market is the, "EZZZ SWING," Bedside Awing Arm, Part No. QA01, Quality of Life, Inc. of Minnetrista, MN, which has a post mounted on a bed and a gooseneck near the top with a Velcro tab to secure the air hose.

The problem of maintaining an open breathing line and minimizing the stress on the mask and the wearer's head has been addressed in other prior art patents, for example, Koncsek, U.S. Pat. No. 5,836,361, Harmon, U.S. Pat. No. 5,279,486, and Dvorachek, U.S. Pat. No. 4,238,096 with varying degrees of success.

What is needed in the art is a low cost, simple support system that can be easily assembled and disassembled for travel and provides a variable position for the mask without becoming entangled with the user or the bedclothes.

SUMMARY OF THE PRESENT INVENTION

Therefore, an objective of this invention is to provide a system for treating sleep apnea that removes the breathing hose from contact with the user and the bed while providing a variable position for the hose to compensate for movement of the user.

It is another objective of this invention to provide a support post and cantilever arm coupled by a spring biased pulley to control the position of the hose.

It is a further objective of this invention to provide the components with structure permitting manual assembly and disassembly without the use of tools. The components are also formed to be reduced in size for ease of packing.

SHORT DESCRIPTION OF THE DRAWINGS

FIG. 1 is a side view of the assembled support of this invention without the air hose;

FIG. 2 front view of the support of this invention;

FIG. 5 is a side view of the base with a leg of this invention;

FIG. 6 is a top view of a hose clamp of this invention; and

FIG. 7 is a top view of a storage stay of this invention.

DETAILED DESCRIPTION OF THE INVENTION

A CPAP machine is normally placed near the user's bed and a length of breathing hose extends from the machine to a mask worn by the user while asleep. The breathing hose has sufficient length to allow for movement of the wearer during the night however, the hose has a tendency to become entangled in the bedclothes and wrap around the wearer.

Figure 1:
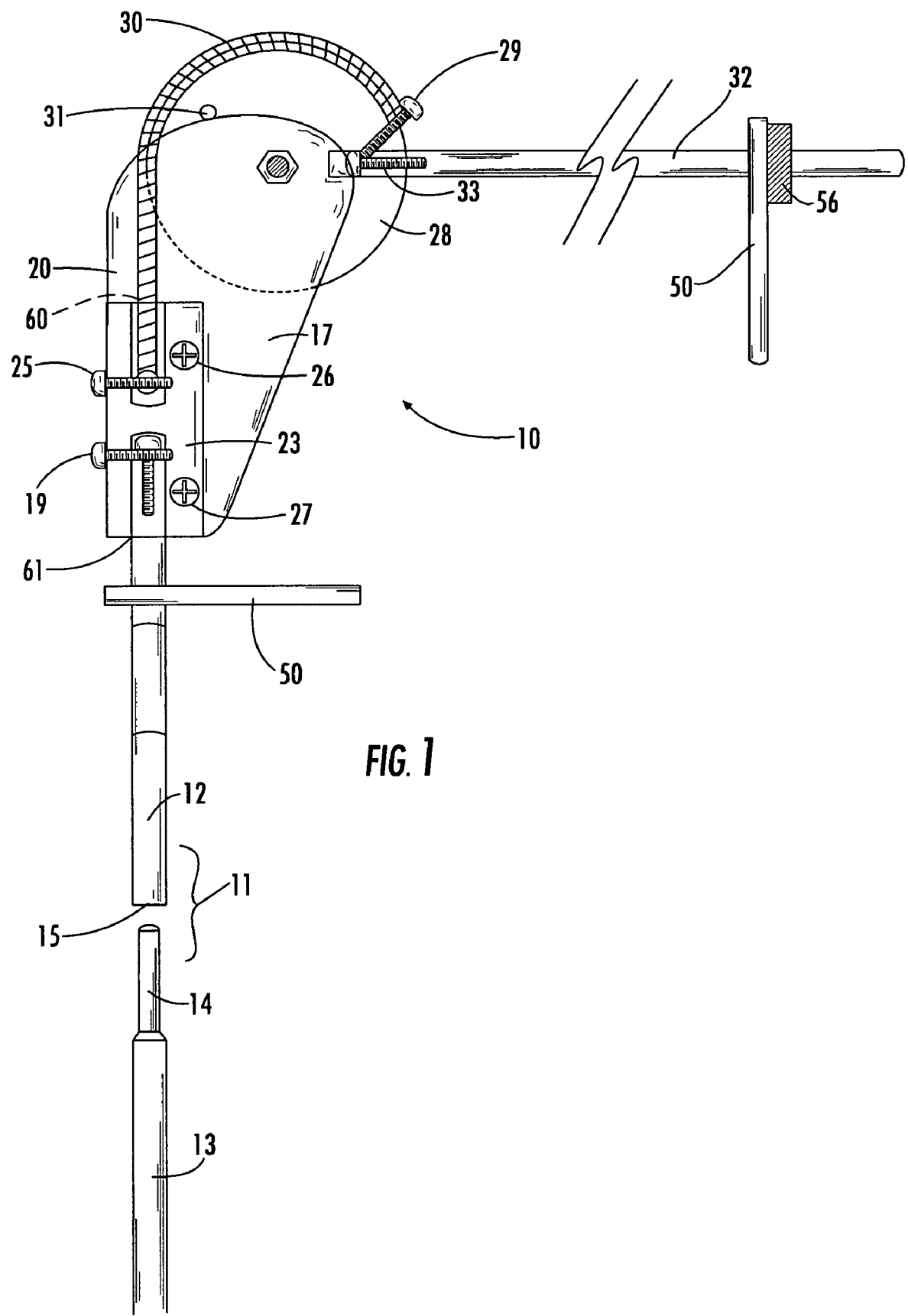
Figure 2:
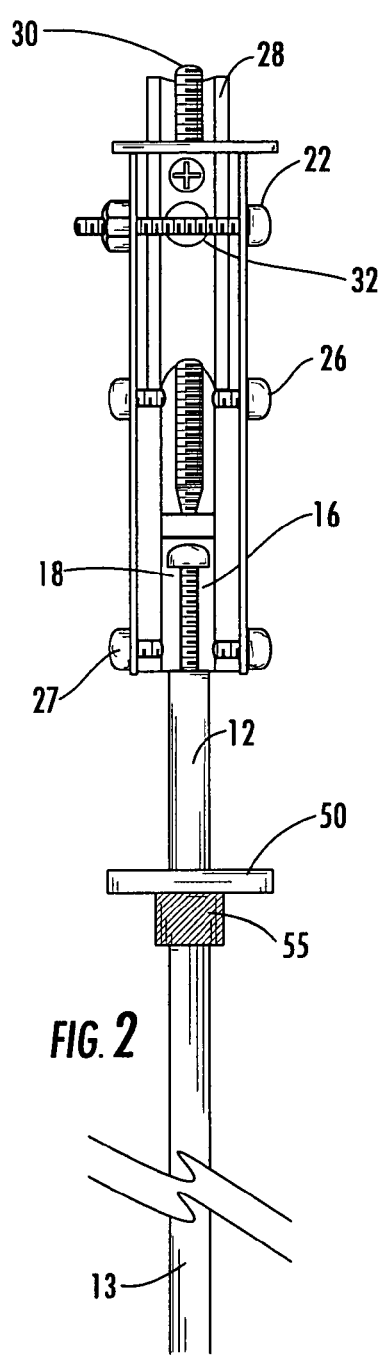

The comfort enhancer 10, shown in FIG. 1, provides flexible support for the breathing hose of a CPAP machine (not shown). A support post 11 is spaced laterally from a bed and extends perpendicularly above the bed to a height to clear the normal turning of a sleeping wearer. The support post may be in separate sections 12 and 13, as shown, with male 14 and female 15 fittings or a telescoping tube or hinged. A hose clamp 50 is slidably mounted on the support post. In FIG. 2, a hose clamp collar 55 is frictionally mounted on the support post. The position of the hose clamp 50 may be adjusted by moving the hose clamp collar 55 to the desired location. The top end 16 of the post is connected to a bracket 17 by inserting the end into a cavity 18. The end 16 is secured to the bracket by a set screw 19 threaded through the wall of the cavity and contacting the end of the post.

Figure 3:
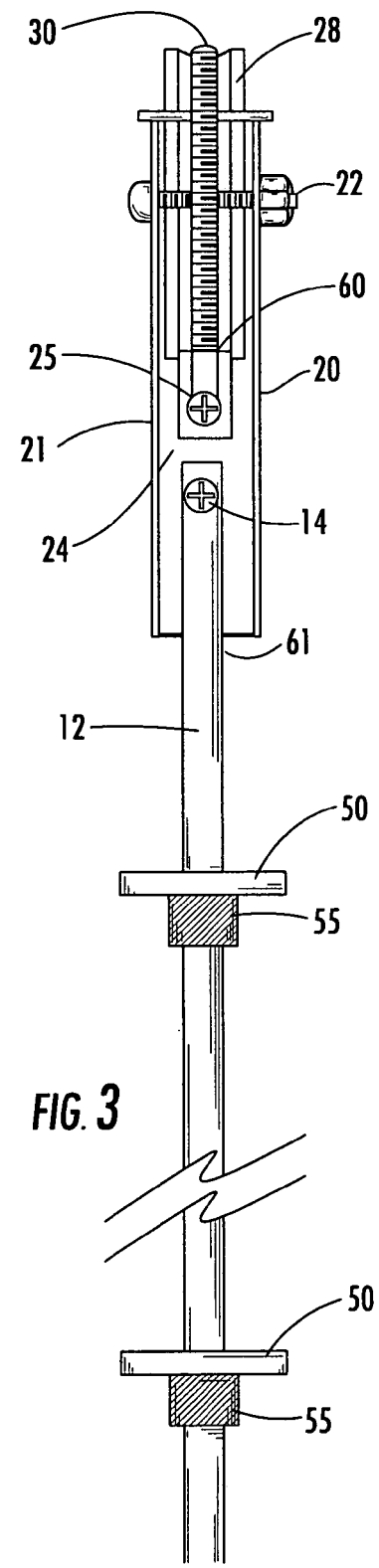
FIG. 3 is a back view of the support of this invention.

The bracket 17 is composed of two parallel planar sides 20 and 21 connected by an axle 22 and a rectangular insert 23. The edge 24 of the insert has a threaded hole for the set screw 19 and a threaded hole for the spring screw 25, as shown in FIG. 3. The sides of the insert are attached to the bracket by screws 26 and 27. The top end of the insert 23 has a bore 60 for insertion of the coil spring 30. The bottom end of the insert has a bore 61 for insertion of the support post 11.

A pulley 28 is rotatably mounted on the axle 22. A spring retainer is fixed to the circumference of the pulley by screw 29. A coil spring 30 extends from the spring screw on the bracket to the spring retainer on the pulley 28. The coil spring 30 maintains a spring bias on the rotation of the pulley 28 to return to its original position after rotation. The pulley 28 has a pin stop 31 on one side to engage the bracket 17 in the original position and limit spring biased return rotation. The spring bias may be generated by other types of springs acting between the pulley and the bracket. The spring tension generated by the rotation of the pulley need not be high but enough to prevent slack in the breathing tube.

A cantilever arm 32 is attached at one end 33 about the circumference of the pulley 28, as shown in FIG. 2, to extend generally normal to the support post 11 and parallel to the bed above the sleeping user. A hose clamp 50 and hose clamp support 56 are slidably connected to the arm to initially adjust the hose toward the vertical between the mask and the hose clamp. In this manner, the weight of the hose is compensated for by the spring bias on the pulley which is transferred to the cantilever arm 32. The arm may be one piece, hinged, telescoping tubes, or sections connected by male, female joints.

When the wearer rolls or moves his head away from the post 11, the lever arm 32 will move vertically downwardly and, if necessary, the bracket 17 will rotate on the support post 11 to relieve tension on the hose. As the wearer moves back toward the post, the arm will move upwardly in response to the spring bias to remove slack from the hose.

Figure 4:
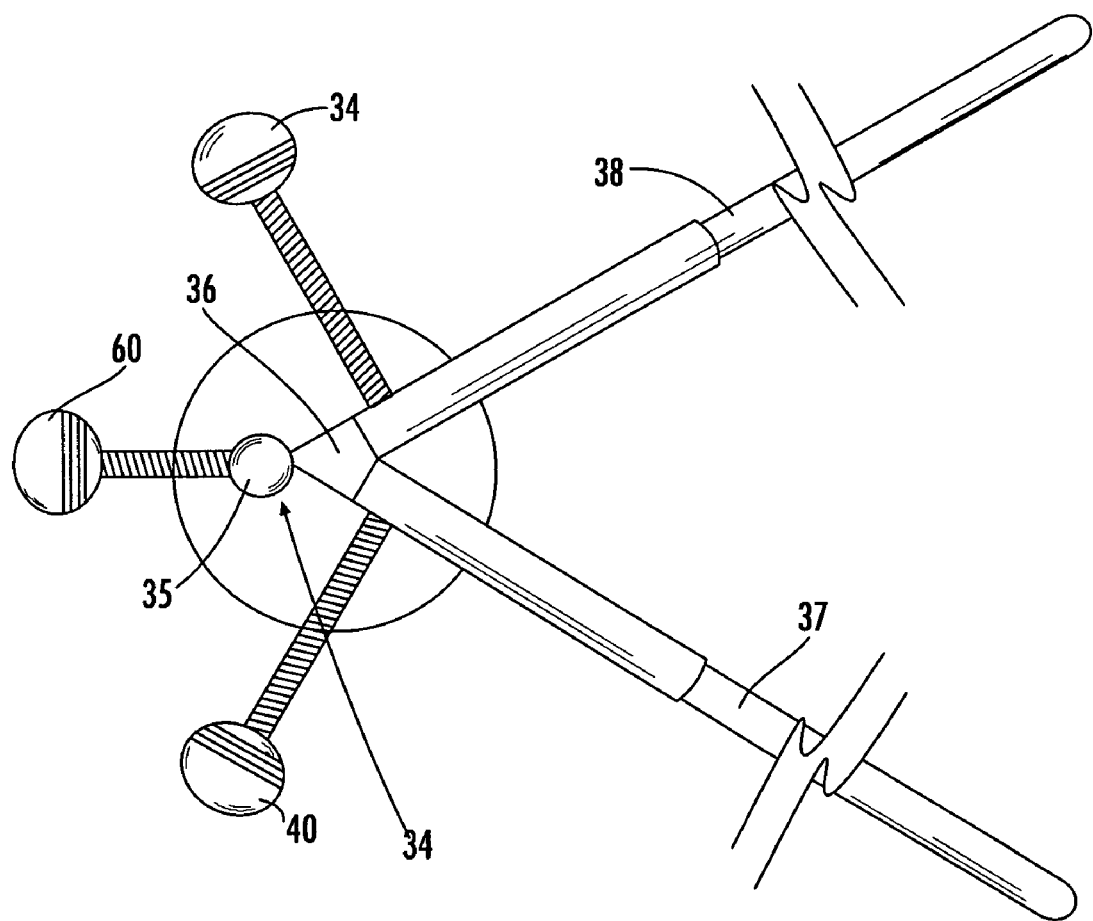
FIG. 4 is a top view of the base of the support of this invention.

The comfort enhancer 10 has a base 34, shown in FIG. 4, that is preferably placed between the mattress and the springs of the bed but may sit on the floor or a table. The base has an aperture 35 and is slidable along the support post 11. The base 34 has a thumbscrew 60 threaded into the aperture 35 to secure the base to the post at the proper height. The base 34 has a bi-pod fixture 36 with a V-shaped passageway to receive two intersecting base legs 37 and 38. The legs 37 and 38 provide stability to the support by increasing the lever arm necessary to pivot the support post. Each passageway has a thumbscrew 39 and 40 to secure the legs to the base. The legs may be one piece, or telescoping tubes, or hinged, or sections connected by male female joints.

The hose clamps 50 have an aperture 51 in one end for insertion of the support post 11 or the cantilever arm 32. The other end of the clamp is formed with two resilient arms 52 and 53 for frictionally holding the breathing tube. The open arms allows the hose to separate from the clamps in the event of a sudden and/or forceful pull on the hose.

The comfort enhancer is designed to be collapsible for ease in traveling and storage. The components may be assembled and disassembled by hand. Several storage stays 54 can be included. The stays have an elongated flat body with apertures 57 and 58 in each end. One stay is slidably mounted on support post 12 by aperture 57. The disassembled support post and cantilever arm may be linked together by inserting the cantilever arm in the aperture 58 of the stay to minimize space requirements.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A support kit for a breathing hose comprising a base for contacting a bed, a post having a top end, a bottom end and being adjustable in length, said bottom end of said post adapted to be removably attached to said base normal to said bed, a first hose clamp slidably affixed to said post adapted to engage a breathing hose, a bracket adapted to be connected to said top end of said post, said bracket including a pulley mounted to rotate in a plane parallel with said post, said pulley having a circumferential groove, a spring attached at one end to said bracket and disposed in said groove, the other end of said spring attached to said pulley whereby rotation of said pulley lengthens said coil spring and applies spring bias to said pulley, a fastener on said periphery of said pulley for securing a cantilever arm, said cantilever arm adapted to extend from said fastener normal to said post, and a second hose clamp adapted to be adjustably affixed to said cantilever arm whereby said kit may be assembled and support a breathing hose spaced apart from a bed.

2. A support kit for a breathing hose of claim 1 comprising said base including a plate adapted to be disposed beneath a mattress, an aperture in said plate sized to slide along said post, a first fastener adapted to block said aperture to lock said plate at a position on said post, a bi-pod fixture mounted on said plate, at least two legs adapted to connected to said bi-pod fixture normal to said post.

3. A support kit for a breathing hose of claim 1 comprising said post having a plurality of sections, said sections being telescopically connected to each other.

4. A support kit for a breathing hose of claim 1 comprising said bracket having spaced apart opposed sides, an axle connecting said sides, said pulley rotating about said axle, a connector disposed between said opposed sides for receiving said top end of said post, and a fastener attached to said connector for securing said post in said connector.

5. A support kit for a breathing hose of claim 4 comprising a coil spring having one end attached to said bracket and the other end attached to said pulley, said pulley having a circumference, said coil spring disposed about said circumference whereby rotation of said pulley lengthens said coil spring and applies spring bias to said pulley.

6. A support kit for a breathing hose comprising a base for contacting a bed, a post having a top end, a bottom end and being adjustable in length, said bottom end of said post adapted to be removably attached to said base normal to said bed, said a first hose clamp slidably affixed to said post adapted to engage a breathing hose, a bracket adapted to be connected to said top end of said post, said bracket including a pulley mounted to rotate in a plane parallel with said post, a spring attached to said bracket and to said pulley biasing the rotation of said pulley, a fastener on said periphery of said pulley for securing a cantilever arm, said cantilever arm adapted to extend from said fastener normal to said post, and a second hose clamp adapted to be adjustably affixed to said cantilever arm whereby said kit may be assembled and support a breathing hose spaced apart from a bed, said bracket having spaced apart opposed sides, an axle connecting said sides, said pulley rotating about said axle, a connector disposed between said opposed sides for receiving said top end of said post, and a fastener attached to said connector for securing said post in said connector, a coil spring having one end attached to said bracket and the other end attached to said pulley, said pulley having a circumference, said coil spring disposed about said circumference whereby rotation of said pulley lengthens said coil spring and applies spring bias to said pulley, a spring stop mounted on said pulley and extending outwardly therefrom, said spring stop engaging an opposed side of said bracket when said spring is unbiased.

7. A support kit for a breathing hose of claim 6 comprising said base including a plate adapted to be disposed beneath a mattress, an aperture in said plate sized to slide along said post, a first fastener adapted to block said aperture to lock said plate at a position on said post, a bi-pod fixture mounted on said plate, at least two legs adapted to connected to said bi-pod fixture normal to said post.

8. A support kit for a breathing hose of claim 6 comprising said post having a plurality of sections, said sections being telescopically connected to each other.

* * * * *